(12) United States Patent
Pischel et al.

(10) Patent No.: US 6,342,631 B1
(45) Date of Patent: Jan. 29, 2002

(54) METHOD OF PRODUCING CALCIUM PYRUVATES

(75) Inventors: Ivo Pischel, Tacherting; Stefan Weiss, Trostberg; Gunter Ortenburger, Trostberg; Harro Konig, Trostberg, all of (DE)

(73) Assignee: SKW Trostberg Aktiengesellschaft, Trostberg (DE)

( * ) Notice: Subject to any disclaimer, the term of this patent is extended or adjusted under 35 U.S.C. 154(b) by 0 days.

(21) Appl. No.: 09/651,638

(22) Filed: Aug. 30, 2000

Related U.S. Application Data

(60) Continuation of application No. 09/163,117, filed on Sep. 29, 1998, now abandoned, which is a division of application No. 08/955,838, filed on Oct. 21, 1997, now Pat. No. 5,962,734.

(30) Foreign Application Priority Data

Jul. 11, 1997 (DE) .......................................... 197 29 786

(51) Int. Cl.⁷ ............................................. C07C 59/147
(52) U.S. Cl. ......................................... 562/577; 514/23
(58) Field of Search ............................. 514/23; 562/577

(56) References Cited

U.S. PATENT DOCUMENTS

| | | | | |
|---|---|---|---|---|
| 5,294,641 A | | 3/1994 | Stanko | 514/423 |
| 5,395,822 A | | 3/1995 | Izumi et al. | 514/557 |
| 5,480,909 A | | 1/1996 | Stanko | 514/423 |
| 5,612,237 A | | 3/1997 | Stanko et al. | 514/557 |
| 5,716,926 A | | 2/1998 | Beale et al. | 514/3 |
| 5,723,661 A | * | 3/1998 | Zimmermann et al. | |
| 5,756,469 A | * | 5/1998 | Beale et al. | |

FOREIGN PATENT DOCUMENTS

| | | |
|---|---|---|
| EP | 0795534 | 9/1997 |
| FR | 1465432 | 3/1967 |
| GB | 2313544 | 3/1997 |

* cited by examiner

*Primary Examiner*—Gary Geist
*Assistant Examiner*—Hector M Reyes
(74) *Attorney, Agent, or Firm*—Fulbright & Jaworski LLP

(57) ABSTRACT

A method of producing calcium pyruvates is described, in which calcium salts of organic acids or acidic organic keto or hydroxy compounds are reacted with pyruvic acid at a temperature in the range from −20 to +120° C., if necessary in the presence of a solvent or diluent. In this way, high-purity calcium pyruvates are obtained which can be largely free of water and have a very long shelf life.

4 Claims, No Drawings

METHOD OF PRODUCING CALCIUM PYRUVATES

This is a continuation of U.S. patent application Ser. No. 09/163,117 filed Sep. 29, 1998, abandoned, which is a divisional of U.S. patent application Ser. No. 08/955,838 filed Oct. 21, 1997, now U.S. Pat. No. 5,962,734.

This invention relates to a method of producing calcium pyruvates which is especially suitable for the production of very pure and largely anhydrous calcium pyruvate salts, as well as to novel calcium pyruvate salts and the use thereof, especially as a component of physiologically compatible compositions.

It is a known fact that salts of pyruvic acid (pyruvates) have valuable physiological, therapeutic and dietetic properties. Pyruvates, especially calcium pyruvates, are used to enhance long-term performance and strength in the field of sport, to reduce weight and body-fat in the field of health care, where it is also used as a protective substance for body cells and tissues (in particular for cardiovascular, hepatic, nephrotic, peritoneal and neuronal tissue), as a substance which inhibits the formation of free radicals and as a substance which scavenges free radicals in body cells and tissues (including synovial tissue). Pyruvates are also used as food supplements, wound-healing agents and for the treatment of kidney diseases (acute kidney failure and nephrolithiasis).

Of the pyruvate salts, sodium and potassium pyruvates, however, are little suited for therapeutic applications or as food supplements on account of their sodium- and potassium-ion content. In contrast to alkali-metal ions, calcium ions do not result in any physiological side effects, which means that calcium pyruvates can safely be used for therapeutic purposes and as a food supplement.

There are only two methods which have been described so far in the prior art for producing calcium pyruvates. According to the article published by K. Jowanowitsch in "Monatshefte" Nr. 6, pp. 467–476 (1885), tartaric acid in glycerin is dehydrated or decarboxylated to a glycidyl pyruvate, which subsequently reacts with lime in aqueous solution to form calcium pyruvate. As was established by proceeding according to the examples contained in this publication, this process does not result in the formation of calcium pyruvates but of polymeric pyruvic acid derivatives.

According to French patent no. 1 465 432, calcium pyruvate is obtained by neutralizing pyruvic acid with calcium carbonate, hydroxide or oxide in water. The disadvantage of this method is the fact that only impure or unstable calcium pyruvates are obtained, which contain more than 2.5 mol water of crystallization and occur in the form of 2,2-dihydroxypropionate ions. These reaction products as a rule contain little calcium pyruvate and comparatively large quantities of by-products, since the pyruvic acid or pyruvate ion reacts by way of aldol addition or aldol condensation to form acyclic or cyclic dimers and polymers of pyruvic acid. With respect to acyclic compounds, particular mention is made here of para-pyruvic acid (4-hydroxy-4-methyl-2-oxoglutaric acid) and its salts, and of the higher aldol-addition products. Oxalic acid and methyl succinic acid may also form as by-products.

By way of lactonization, ketalization, and other reactions, the acyclic pyruvicacid polymers can, in turn, form cyclic compounds such as 2-hydroxy-2methyl-4-oxoglutaric acid-5-lactone and derivatives of trimesic, isophthalic and pyran tricarboxylic acids. These by-products can form in a similar way when calcium pyruvates containing more than 2.5 mol water of crystallization are stored.

The calcium pyruvates known from the prior art are thus not suitable for therapeutic uses (free-radical scavenger, cellular protection, obesity etc.) or as a food supplement, because during production and storage of these pyruvates by-products and decomposition products of pyruvic acid and its salts are which may be physiologically incompatible or even toxic.

The object of this invention was thus to develop a method of producing calcium pyruvates which does not have the disadvantages of the methods known from the prior art, and with which high-purity calcium pyruvates with a long shelf life are obtained, which are largely free of by-products that might have a toxicological effect.

This object was established according to the invention by reacting calcium salts of organic acids or acidic organic keto or hydroxy compounds with pyruvic acid at a temperature in the range from −20 to +120° C., if necessary in the presence of a diluent or solvent.

Surprisingly, it was found that high-purity, largely anhydrous calcium pyruvates are obtained in this way. Calcium pyruvates produced in this way are also thermostable, and have a very long shelf life. This is surprising, because pyruvic acid is a relatively unstable compound, and hitherto-known calcium pyruvates decomposed within a short time to dimeric and polymeric derivatives of pyruvic acid.

According to the method of this invention, as indicated above, calcium salts of organic acids or acidic organic keto or hydroxy compounds are reacted with pyruvic acid at a temperature in the range from −20 to +120° C., preferably from 10 to 60° C. Suitable organic acids include, for example, aliphatic monocarboxylic acids which may also bear substituents such as OH—, CO—, CN—, Cl— or Br— groups, and which can also be mono- or polyunsaturated. Examples of such monocarboxylic acids are formic acid, acetic acid, propionic acid, butyric acid and lactic acid. For the method of the invention, use can also be made of aliphatic di- and tricarboxylic acids; these can likewise be mono- or polyunsaturated and may also bear substituents such as OH— groups. Examples of such acids are citric acid, tartaric acid, succinic acid, maleic acid, fumaric acid and malic acid. Instead of organic acids, use can also be made of acidic organic keto or hydroxy compounds, such as ascorbic acid. These calcium salts can be used in the anhydrous form, as hydrates or as wet products, Particular preference is given to physiologically compatible compounds which are approved by food law.

According to the method of the invention, the pyruvic acid, too, can be used in the anhydrous form, in aqueous solution, or dissolved or suspended in an organic solvent or diluent. The scope of the invention also provides for production of the pyruvic acid in situ, i.e. as an intermediate, for example by reacting an alkali-metal pyruvate such as sodium or potassium pyruvate with an organic acid such as sulfuric or hydrochloric acid at a temperature in the range from −20 to +90° C., preferably −10 to +60° C.

Suitable solvents or diluents for the method of the invention are water and/or organic solvents such as alcohols (methanol, ethanol, isopropanol, cyclohexanol), ethers (diethyl ether, tetrahydrofuran, 1,4-dioxane), ketones (acetone, methyl ethyl ketone, cyclohexanone), esters (methyl acetate, ethyl acetate, ethyl formate), organic acids (formic, acetic, propionic, lactic and pyruvic acids), nitrites (acetonitrile) as well as aliphatic (pentane, hexane, cyclohexane) and aromatic (toluene) hydrocarbons. However, it is also quite possible to react the organic calcium salts with pyruvic acid in the absence of solvents or diluents.

The ratio of organic calcium salt to pyruvic acid can be varied within wide limits; suitable molar ratios can range, for example, from 10:1 to 1:20, preferably from 5:1 to 1:10. However, it has proved to be of particular advantage if the organic calcium salts and the pyruvic acid are made to react in stoichiometric or approximately stoichiometric ratios, e.g. in a molar ratio of 2:1 to 1:4.

The reaction of the invention is largely unproblematic to carry out, and is conducted using common techniques and customary technical apparatus such as kneaders, mixers, blade dryers and agitating vessels.

In this manner a high yield (>95%) of high-purity (>97%) calcium pyruvates is obtained without the need for any time-consuming purification steps. Of particular importance is the fact that the method of the invention allows the preparation of novel calcium pyruvates which are not only very pure but have a very long shelf life and, in addition, are largely anhydrous and have the following structural formula:

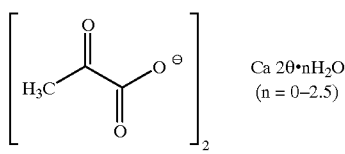

As was established by means of IR-spectroscopic examination, the calcium pyruvates produced according to the invention, which contain 2.5 mol or less water of crystallization, are obtained mainly as the 2-oxo-propionate ion.

By virtue of their high level of purity and very good storage properties, the calcium pyruvates produced according to the method of the invention are excellently suited as components of physiologically compatible compositions, e.g. for applications in the field of medicine and as food supplements.

The calcium pyruvates produced according to the invention can thus be used together with at least one other physiologically compatible substance selected, for example, from the group comprising pharmaceutical active ingredients, pharmaceutical adjuvants and carriers, vitamins, mineral substances, carbohydrates and other food supplements to make up physiologically compatible compositions.

These calcium pyruvates are particularly suitable in the field of sport for enhancing long-term performance and strength, in the field of health care for reducing weight and body-fat, as a protective substance for body cells and tissues (especially cardiovascular, hepatic, nephrotic, peritoneal and neuronal tissue) and as a substance which inhibits the formation of free radicals and which scavenges free radicals in body cells and tissues (including synovial tissue), and also for treating obesity and weight problems and as a food supplement.

The following examples serve to explain the invention in more detail:

EXAMPLE 1

81 g (0.46 mol) of calcium acetate monohydrate are added over a period of 1 hour at 20° C. to a solution of 88 g (1 mol) of pure pyruvic acid (99%) in 400 ml of ethyl acetate and stirred for 18 hours. The calcium pyruvate formed is subsequently vacuum-filtered and washed with 2×250 ml of ethyl acetate. The yield of calcium pyruvate monohydrate is 102 g (95% of the theoretical yield).

$(C_3H_3O_3)_2Ca \times 1H_2O$, calculated: C 31.04%, H 3.47%, Ca 17.26%; found: C 31.19%, H 3.58%, Ca 17.20%; MP >300° C.; IR (KBr) [1/cm]: 634, 742, 832, 1185, 1354, 1402, 1643, 1713, 3195, 3480[1]; H-NMR ($D_2O$, 300 MHz): δ=2.36 (s, 3H, $CH_3$—CO), 1.49 (s, 3H, $CH_3$—$C(OH)_2$); HPLC content (calcium pyruvate): 92.1%=99.8% calcium pyruvate monohydrate.

EXAMPLE 2

9.5 g of water are added to a solution of 45.5 g (0.5 mol) of 98.7% pyruvic acid in 200 ml of glacial acetic acid and, over a period of one hour at 40° C., 41.8 g (0.25 mol) of calcium acetate semihydrate are added. The mixture is stirred at 40° C. for a further 3 hours, then cooled to 15° C. and agitated for another hour. The calcium pyruvate is then vacuum-filtered, washed with 2×100 ml of ethyl acetate and dried at 50° C. and 15 mbar. The yield of calcium pyruvate monohydrate is 55 g (95% of the theoretical yield).

EXAMPLE 3

At a temperature of 15 to 20° C. and over a period of 45 minutes 64.3 g (0.49 mol) of 70% sulfuric acid is added dropwise to a suspension of 110 g (1 mol) of sodium pyruvate in 200 ml of ethyl acetate. After 3 hours the precipitated sodium sulfate is vacuum-filtered and washed with 2×40 ml of ethyl acetate. 250 g of concentrated acetic acid are added to the filtrate, and the mixture heated to 35° C. Within a period of 30 minutes, 80.2 g (0.48 mol) of calcium acetate semihydrate are added. The low-viscosity suspension is stirred for a further 3 hours, after which the calcium pyruvate is vacuum-filtered and washed with 2×100 ml of ethyl acetate. The product is dried to constant weight at 50° C. in a vacuum-drying chamber. The yield of calcium pyruvate monohydrate is 107 g (96% of the theoretical yield).

EXAMPLE 4

In a laboratory kneader, 88 g (1 mol) of pyruvic acid are added at 20° C. and over a period of 30 minutes to 84 g (0.5 mol) of calcium acetate semihydrate, and kneaded for 2 hours. The calcium pyruvate, damp with acetic acid, is then dried at 50° C. and 12 mm Hg in a vacuum-drying chamber. The yield of calcium pyruvate semihydrate is almost quantitative (>99% of the theoretical yield).

EXAMPLE 5

20 g of water are added to a solution of 45.5 g (0.5 mol) of 98.7% pyruvic acid in 200 ml of glacial acetic acid and, over a period of one hour at 40° C., 32.5 g (0.25 mol) of calcium formate are added. The mixture is agitated at this temperature for 3 hours, then cooled to 15° C. and agitated for another hour. The calcium pyruvate is then vacuum-filtered, washed with 2×100 ml of ethyl acetate and dried at 50° C. and 15 mbar. The yield of calcium pyruvate trihydrate is 65 g (97% of the theoretical yield)

$(C_3H_3O_3)_2Ca \times 3H_2O$, calculated: C 26.87%, H 4.51%, Ca 14.94%; found: C 26.77%, H 4.53%, Ca 14.70%; MP >300° C.; IR (KBr) [1/cm]: 668, 789, 862, 934, 965, 1142, 1182, 1408, 1610, 3430[1]; H-NMR ($D_2O$, 300 MHz): δ=2.36 (s, 3H, $CH_3$—CO), 1.49 (s, 3H, $CH_3$—$C(OH)_2$); HPLC content (calcium pyruvate): 79.4%=99.4% calcium pyruvate trihydrate.

EXAMPLE 6 (Comparison)

Use of the method described in "Monatshefte" 6, 467–476 (1885) (K. Jowanowitsch)

A mixture of 40 g of glycerin and 32 g of tartaric acid is heated to 140° C. until no more steam escapes. Then the mixture is heated to 260° C., being subjected to fractional distillation. The first fraction is a low-viscosity emulsion from which 0.2 g of a crystalline solid separate out. This solid is shown by NMR, IR and GC-MS analyses to be glycidyl pyruvate. It is dissolved in its entirety in 5 ml of water, and after addition of 80 mg of calcium carbonate the mixture is heated and made to boil for 30 minutes. Once the excess calcium carbonate has been removed, the aqueous solution is analyzed by HPLC chromatography. However, no calcium pyruvate can be detected.

What is claimed is:

1. Calcium pyruvate of the formula $(CH_3COCOO^-)_2 Ca^{2\oplus} \cdot nH_2O$ where n is less than 2.5.

2. Physiologically compatible compositions comprising the calcium pyruvate of claim 1 and at least one other physiologically compatible substance selected from the group consisting of pharmaceutically active ingredients, pharmaceutical adjuvants, pharmaceutical carriers, vitamins, mineral substances, carbohydrates and food supplements.

3. The calcium pyruvate of claim 1, wherein n=1.

4. The calcium pyruvate of claim 1, wherein n=0.5.

* * * * *